US006176838B1

United States Patent
Sase

(10) Patent No.: US 6,176,838 B1
(45) Date of Patent: Jan. 23, 2001

(54) METHOD AND APPARATUS FOR MEASURING HEPATIC BLOOD FLOW AMOUNT

(75) Inventor: Shigeru Sase, Narashino (JP)

(73) Assignee: Anzai Medical Kabushiki Kaisha, Tokyo (JP)

(*) Notice: Under 35 U.S.C. 154(b), the term of this patent shall be extended for 0 days.

(21) Appl. No.: 09/271,253

(22) Filed: Mar. 17, 1999

(30) Foreign Application Priority Data

Jan. 29, 1998 (JP) .................................................. 10-17433

(51) Int. Cl.[7] .......................................................... A61B 5/00
(52) U.S. Cl. ............................................. 600/604; 600/431
(58) Field of Search ................................... 600/504, 505, 600/431

(56) References Cited

U.S. PATENT DOCUMENTS

| | | | | |
|---|---|---|---|---|
| 3,890,959 | * | 6/1975 | Youdin et al. ........................ | 600/431 |
| 4,718,432 | * | 1/1988 | Kimura et al. ........................ | 600/431 |
| 5,271,401 | * | 12/1993 | Fishman ................................ | 600/431 |
| 5,357,959 | * | 10/1994 | Fishman ................................ | 600/420 |
| 5,402,785 | * | 4/1995 | Leigh et al. ........................... | 600/419 |

FOREIGN PATENT DOCUMENTS

| | | |
|---|---|---|
| 3522113 A1 | 1/1986 | (DE) . |
| 0 370 636 A1 | 5/1990 | (EP) . |
| 0 551 898 A1 | 7/1993 | (EP) . |

OTHER PUBLICATIONS

David Gur et al., "Blood Flow Mapping in the Human Liver by the Xenon/CT Method", Journal of Computer Assisted Tomography, 9(3), pp. 447–450 May/Jun. 1985.
Hiroki Taniguchi et al., "Analysis of Models for Quantification of Arterial and Portal Blood Flow in the Human Liver Using PET", Journal of Computer Assisted Tomography, 20(1), pp. 135–144, 1996.
(NOTE: In relation to DE 3522113 A1, see enclosed European Search Report.)
Hiroko Taniguchi et al., "Eizojoho Medical", Industrial Development Organization (Sangyo Kaihatsukiko, Inc.) Co., Ltd., vol. 26, No. 8, Apr. 1994, pp. 449–453.

* cited by examiner

Primary Examiner—Robert L. Nasser
(74) Attorney, Agent, or Firm—Paul A. Guss

(57) ABSTRACT

In order to easily measure the hepatic arterial blood flow amount and the portal blood flow amount flowing through the liver, a mixed gas supply apparatus is used to supply a mixed gas of xenon gas and oxygen gas to the lung of a specimen for a certain period of time so that the change in xenon concentration in the tissue of the liver of the specimen is measured (detected) while making decomposition into picture elements by using an X-ray CT system. The hepatic arterial blood flow amount and the portal blood flow amount concerning the respective picture elements obtained by the decomposition are determined by using a computer on the basis of the fact that the xenon concentration in the liver tissue is determined by the xenon concentration in the hepatic arterial blood flow and the xenon concentration in the portal blood flow.

13 Claims, 12 Drawing Sheets

METHOD AND APPARATUS FOR MEASURING HEPATIC BLOOD FLOW AMOUNT

BACKGROUND OF THE INVENTION

1. Field of the Invention

The present invention relates to a method and an apparatus for measuring the hepatic blood flow amount. In particular, the present invention relates to a method and an apparatus for measuring the hepatic blood flow amount, which make it possible to easily measure the blood flow amount concerning the hepar (hereinafter simply referred to as the "liver" as well) by utilizing, for example, a xenon gas inhalator and an X-ray CT (computerized tomography) system.

2. Description of the Related Art

A method has been hitherto known, in order to measure the blood flow in the head of a patient. In this method, for example, a mixed gas of xenon gas and oxygen gas, which is fed from a gas inhalator, is allowed to be inhaled by the patient for a certain period of time by using a respiratory mask followed by allowing the patient to inhale normal air, while periodically obtaining tomographic images of the head of the patient as a specimen by using an X-ray CT system, to analyze the tomographic images so that the blood flow in the head of the patient is measured.

That is, according to the measuring method, the mixed gas passes through the lung of the patient, and it is absorbed into the pulmonary artery. The mixed gas passes through the heart, and it flows as an arterial blood flow into the tissue of the head. The mixed gas passes through the head tissue, and it is returned through the venous blood flow to the heart. The mixed gas passes through the heart, and it is returned to the pulmonary vein. During this process, the time-dependent change in xenon concentration in the head tissue is observed by using the X-ray CT system. The observed time-dependent change is compared with an authentic time-dependent change in xenon concentration in the head in which the tissue is normal. Thus, it is possible to diagnose the head of the patient.

The method for measuring the blood flow based on the use of the xenon gas as described above is not limited to the diagnosis of the head, and it can be also applied to normal organs (internal organs) such as the stomach, the intestine, and the pancreas in which arterial blood flow inflows thereinto and venous blood flow outflows therefrom as in the head.

However, when it is intended that the method for measuring the blood flow described above is applied to the liver, it is noted that not only arterial blood flow inflows into the liver. As disclosed in "EIZOJOHO MEDICAL" {issued in April 1994, Volume 26, Number 8, "Method for simultaneously measuring blood flows in hepatic artery and portal vein based on $H_2^{15}O$ intravenous injection method by using positron CT (about local blood flow amount difference in liver region)" (page 449 to page 453, Hiroki TANIGUCHI et al., the First Department of Surgery of Kyoto Prefectural University of Medicine) published by Industrial Development Organization (SANGYO KAIHATSUKIKO INC.) Co., Ltd.}, it is known that portal blood flow, as venous blood flow, which outflows from the stomach, the intestine, the pancreas, and the spleen as the portal internal organs, also inflows into the liver. Therefore, it is impossible to apply the foregoing conventional technique to the measurement of the blood flow amount in the liver.

A method for measuring blood flow amount in the liver is disclosed in "EIZOJOHO MEDICAL" described above. That is, a principle expression is introduced for the amount of blood which inflows and outflows with respect to the liver. The principle expression is solved on the basis of the result of measurement based on the $H_2^{15}O$ intravenous injection method by using the positron CT. Further, the liver is divided into four regions for each of which the total hepatic blood flow amount, the portal blood flow amount (total amount), and the hepatic arterial blood flow amount (total amount) can be measured, with respect to an injured liver and a non-injured liver.

However, in the case of the intravenous injection method based on the use of the positron CT, even when a blood flow image is obtained, it is still difficult to make comparison with an anatomical structure, and hence it is difficult to apply this method to image diagnosis.

SUMMARY OF THE INVENTION

The present invention has been made considering the knowledge and the problem as described above, an object of which is to provide a method and an apparatus for measuring hepatic blood flow amount, which make it possible to measure the hepatic arterial blood flow amount and the portal blood flow amount in a form suitable for diagnosis.

Another object of the present invention is to provide a method and an apparatus for measuring hepatic blood flow amount, which make it possible to detect the portal blood flow amount and the arterial blood flow amount in each of respective regions of liver tissue.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

An embodiment of the present invention will be explained below with reference to the drawings.

Figure 1:
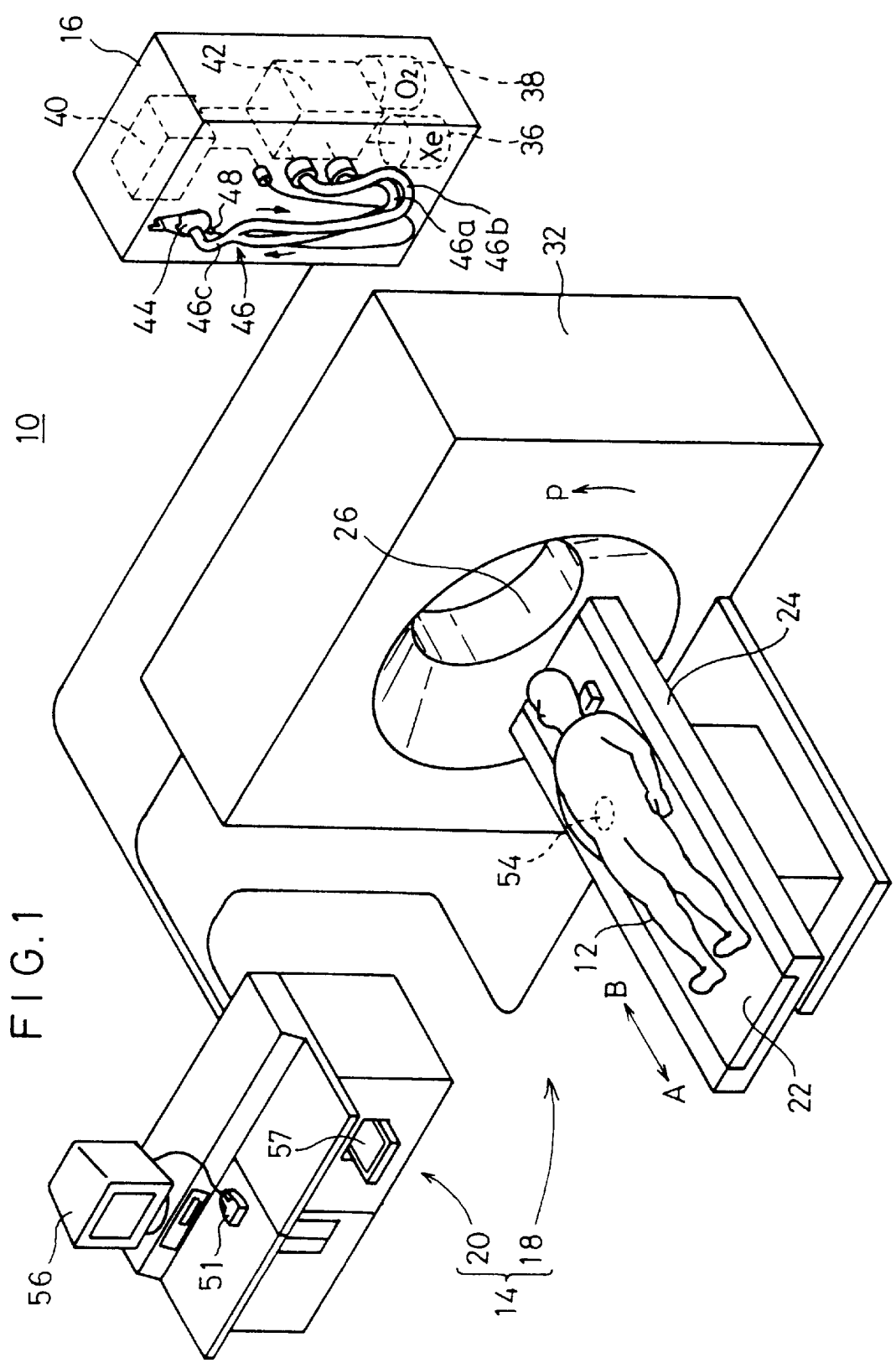
FIG. 1 shows a schematic perspective view illustrating an overall arrangement of an embodiment of the present invention.

FIG. 1 shows a an overall arrangement of an apparatus 10 for measuring the hepatic blood flow amount according to an embodiment of the invention.

Figure 2:
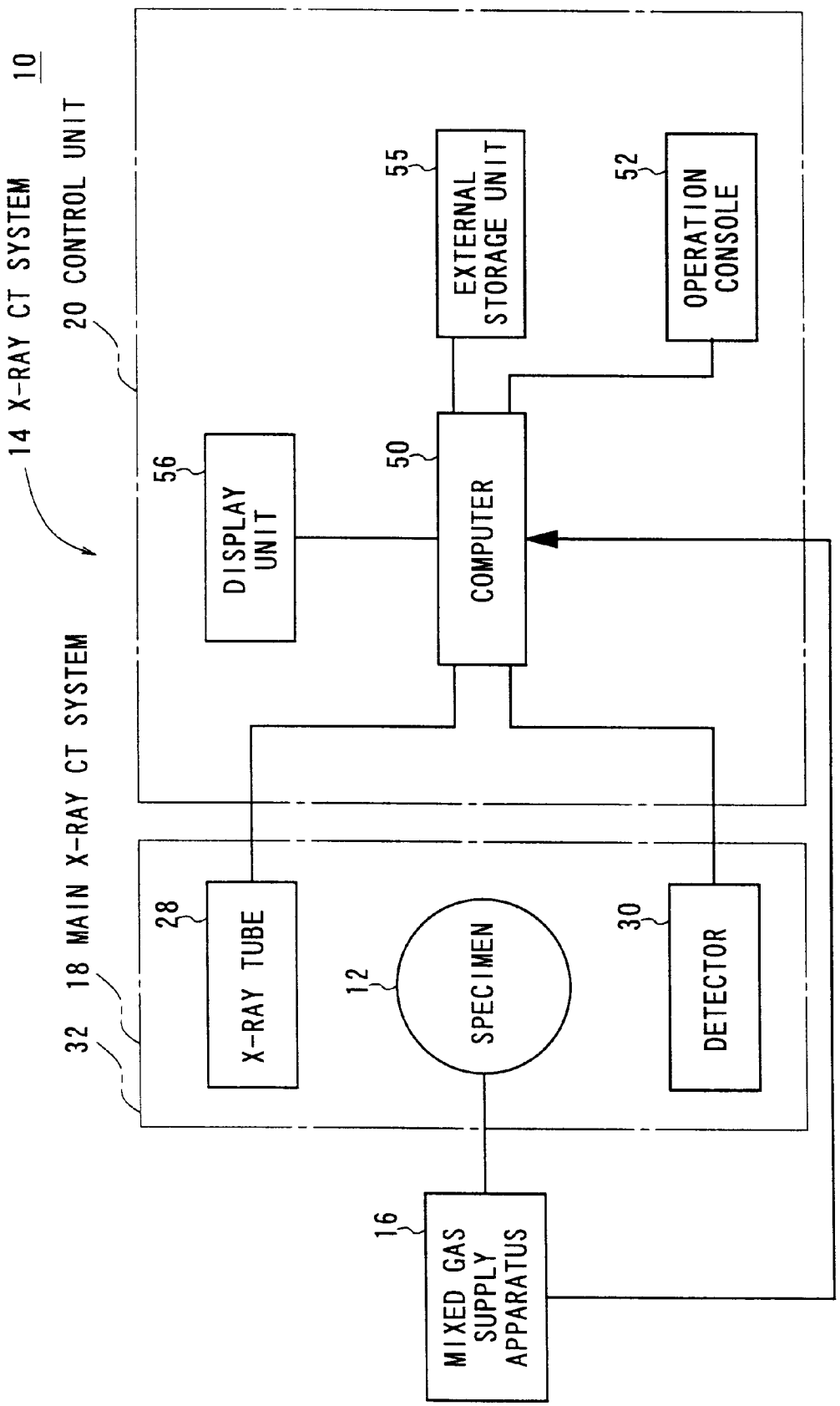
FIG. 2 shows a block diagram illustrating a system of the embodiment of the present invention.

FIG. 2 shows a block diagram of the apparatus 10 for measuring hepatic blood flow amount shown in FIG. 1.

With reference to FIGS. 1 and 2, the apparatus 10 for measuring hepatic blood flow amount basically comprises an X-ray CT system 14 for obtaining a tomographic image of a specimen 12 such as human, and a mixed gas supply apparatus 16 for supplying a mixed gas of xenon (Xe) and oxygen ($O_2$) to the specimen 12. The X-ray CT system 14 comprises a main X-ray CT system 18, and a control unit 20 for controlling the main X-ray CT system 18 and for controlling the mixed gas supply apparatus 16. The control unit 20 also functions as a data-processing unit for processing image data or the like obtained by using the main X-ray CT system 18. The control unit 20 may be arranged such that it is physically divided into a control unit for controlling the main X-ray CT system 18 and a control unit for controlling the mixed gas supply apparatus 16.

The main X-ray CT system 18 is provided with a specimen-placing stand 24 which is arranged, on its top surface, with a movable table 22 for placing the specimen 12 thereon to be moved in directions indicated by the arrows A and B, and a gantry 32 which is formed with a cylindrical opening 26. The gantry 32 is arranged with an X-ray tube 28 (see FIG. 2) which revolves around the cylindrical opening 26 in a direction indicated by the arrow p (see FIG. 1), and a detector 30 which is composed of a plurality of detector elements disposed on the circumference around the opening 26.

The mixed gas supply apparatus 16 includes a xenon gas cylinder 36, an oxygen gas cylinder 38, a main inhalator body 42 for mixing the gases under the control of an internal computer 40, and a conduit 46 having one end connected to the main inhalator body 42 and the other end connected to a respiratory mask 44. In this embodiment, the conduit 46 comprises an intake tube 46a, an expiration tube 46b, and a respiratory mask conduit 46c. A xenon gas concentration-measuring sensor 48 is attached to the respiratory mask 44. A detection signal obtained by the concentration-measuring sensor 48 is supplied to the computer 40 so that the computer 40 calculates the xenon gas concentration in the expiration gas. The computer 40, which controls the overall operation of the mixed gas supply apparatus 16, is electrically connected to the control unit 20 so that they may communicate with each other.

As shown in FIG. 2, the control unit 20 includes a computer 50 which functions as a control unit and a processing unit. The computer 50 is used to control the operation of the main X-ray CT system 18 and the mixed gas supply apparatus 16. The computer 50 also processes the picture element data for constructing the tomographic image of the hepar 54 (hereinafter also referred to as the "liver") of the specimen 12 detected by the detector 30 disposed in the gantry 32 to prepare, for example, the tomographic image. The computer 50 is further connected with an operation console 52 including a mouse 51 and a keyboard, an external storage unit 55 such as a magneto-optical disk unit, and a display unit 56 such as a color CRT (cathode ray tube). In the illustrative apparatus 10 shown in FIGS. 1 and 2, for measuring the hepatic blood flow amount the operation console 52 is practically used such that a mouse pointer, which is displayed on the screen of the display unit 56 and which is operated by using the mouse 51, is manipulated to click on a given display on the screen so that the process indicated by the display is executed. As described later on, for example, the tomographic image (so-called CT image) of the liver 54 represented by the picture element data, which is obtained by the main X-ray CT system 18 by the aid of the computer 50, is displayed in a color or monochromatic illustration on the display unit 56. The image of the liver 54 of the specimen 12, which is subjected to classification into respective areas of the liver tissue through which hepatic arterial blood flow flows and areas of liver tissue through which portal blood flow flows, is also displayed on the display unit 56. The image, which is displayed on the screen of the display unit 56, can be printed out by using a printer contained in the control unit 20 so that the image is outputted as a color or monochromatic hard copy 57 (see FIG. 1).

Next, the operation of the embodiment described above will be explained on the basis of the flow chart shown in FIG. 3. The control entity for the flow chart is the computer 50.

Figure 4:
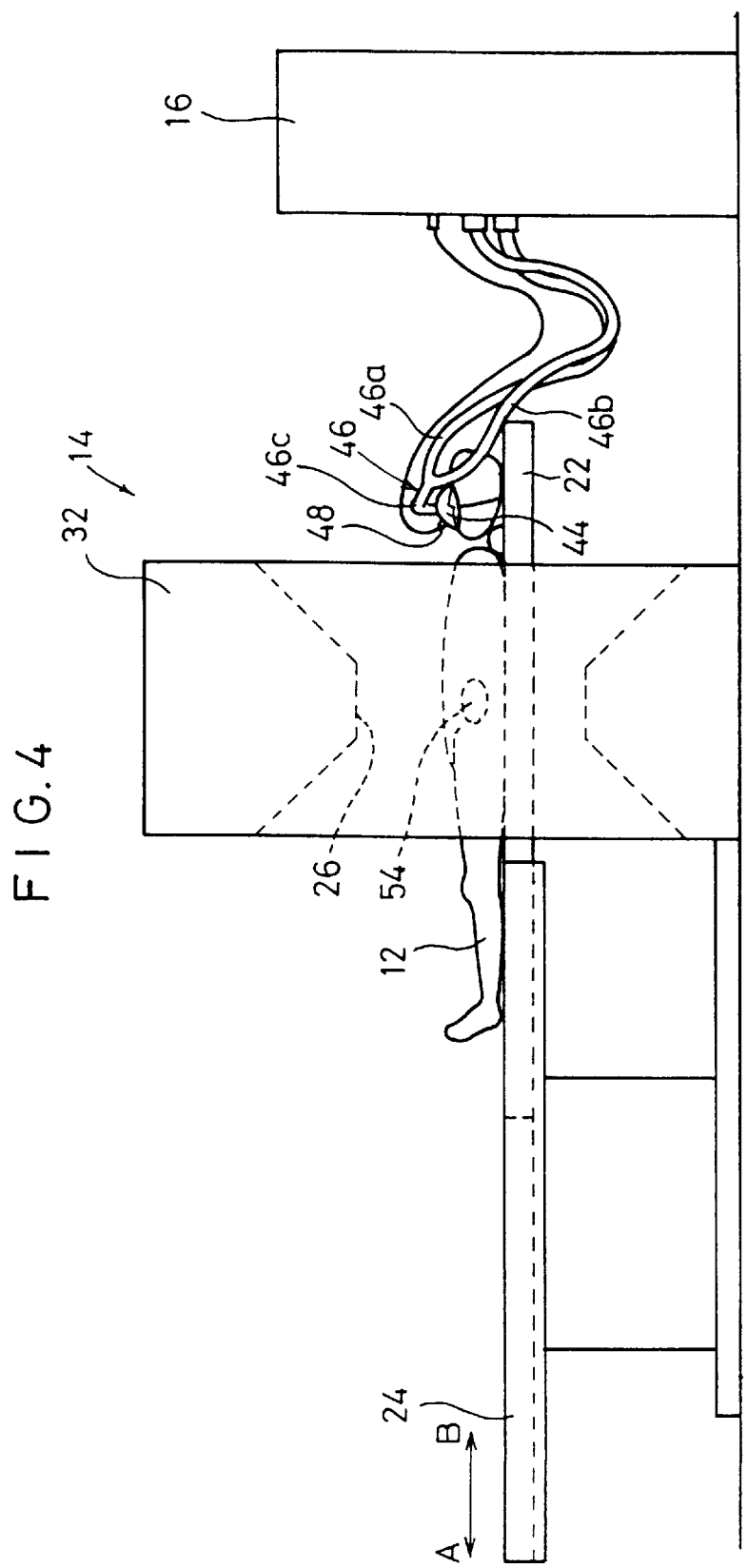
FIG. 4 shows a schematic side view illustrating a state in which a liver of a patient as a specimen supplied with xenon gas is photographed by using an X-ray CT system.

At first, an operator such as a medical doctor operates the operation console 52 so that the movable table 22 is moved in the direction of the arrow B in a state in which the specimen 12 is placed on the specimen-placing stand 24 as shown in FIG. 4. The movable table 22 is stopped at a position at which the liver 54 of the specimen 12 can be photographed to obtain the tomographic image (step S1).

Subsequently, as shown in FIG. 4, the respiratory mask 44 is attached so that the mouth and nose of the specimen 12 are covered therewith (step S2).

The operation console 52 is operated in a state for conducting measurement as shown in FIG. 4. Thus, a measurement start command is sent from the computer 50 of the control unit 20 to the computer 40 of the mixed gas supply apparatus 16, and it is sent to the main X-ray CT system 18 (step S3).

During this process, the tomographic image of the liver 54, i.e., the so-called baseline CT image, is photographed by using the main X-ray CT system 18, and it is incorporated into the external storage unit 55 (step S4).

Subsequently, xenon gas and oxygen gas, which are fed from the xenon gas cylinder 36 and the oxygen gas cylinder 38 respectively, are mixed in a ratio of 30% of xenon gas and 70% of oxygen by using the main inhalator body 42 under the control of the computer 40 of the mixed gas supply apparatus 16. The mixed gas is allowed to pass through the intake tube 46a, the respiratory mask conduit 46c, and the respiratory mask 44, and it is supplied to the lung of the specimen 12. The expiration gas, which is discharged from the lung of the specimen 12, passes through the respiratory mask 44, the respiratory mask conduit 46c, and the expiration tube 46b, and it is returned to the main inhalator body 42. The measurement is started while controlling the mixed gas supply apparatus 16 by the aid of the computer 40 so that the xenon gas concentration in the mixed gas has a predetermined value (30% in this embodiment) from the point of time of the start of the supply of the mixed gas to the specimen 12. Thus, the inhalation process, i.e., so-called Wash-in is started (step S5). For example, an apparatus disclosed by the present applicant in Japanese Patent Publication No. 3-33326 can be used as the mixed gas supply apparatus 16. The xenon gas concentration in the expiration gas is measured at every 40 msec from the point of time of the start of the measurement.

X-ray are radiated onto the specimen 12 from the X-ray tube 28 in the gantry 32 at about every 60 seconds while performing a process to make change to the saturation judgement, the washing process, or the so-called Wash-out process, as described later on, starting from the point of time of the start of intake of the mixed gas with respect to the specimen 12. X-ray, which have passed through the specimen 12, are detected by the detector 30. Thus, the tomographic image of the liver 54 is photographed at about every 60 seconds, and is incorporated as picture element data into the computer 50 (step S6).

Subsequently, the xenon concentration in the liver tissue is calculated for each of the picture elements on the basis of the picture element data (step S7). In this embodiment, the size of the picture element is about 0.5 mm square. However, the size may be changed into any appropriate size. In order to easily understand the present invention, it is conveniently assumed that the phrase "each picture element" referred to in the following description has the same meaning as that of the phrase "each area of tissue or each individual area of tissue" constructing the liver 54.

Accordingly, it is possible to obtain the xenon concentration Ch(t) of each area of liver tissue 54 of the specimen 12, wherein t represents the measurement time in seconds, and has values of about every 60 seconds, for example, t=0, 62, 123, 183, 243, 303, 363, 424, 484, 544, . . . .

If the rate of increase in the xenon concentration Ch(t) in the liver tissue is smaller than a predetermined value having been previously prescribed, then it is judged that the saturated state is achieved (step S8). After it is judged whether or not the washing process is completed (step S9), the supply of the mixed gas is stopped to perform so-called Wash-out in which normal air is fed in place of the mixed gas (step S10).

Further, the process of the step S6 is performed at about every 1 minute, and the process of the step S7 is performed at every 40 ms to complete the washing process. After that (after the judgement in the step S9 is affirmative), the process of the step S6 is performed at about every 1 minute, and the process of the step S7 is performed at every 40 ms in the same manner as described above until the xenon concentration Ch(t) in the liver tissue is not more than the predetermined value (step S11). If the xenon concentration Ch(t) is not more than the predetermined value (step S11: YES), the hepatic arterial blood flow amount and the portal blood flow amount are calculated as explained below (step S12) on the basis of the concentration data of the expiration gas determined by using the xenon gas concentration-measuring sensor 48 and the xenon concentration Ch(t) of the liver 54. Various displays are made on the display unit 56 on the basis of the results of the calculation and other factors as described later on (step S13).

Next, detailed explanation will be made below for the process of the step S12 and its subsequent steps for calculating hepatic arterial blood flow amount and portal blood flow amount for each of respective regions of liver tissue 54.

Figure 5:
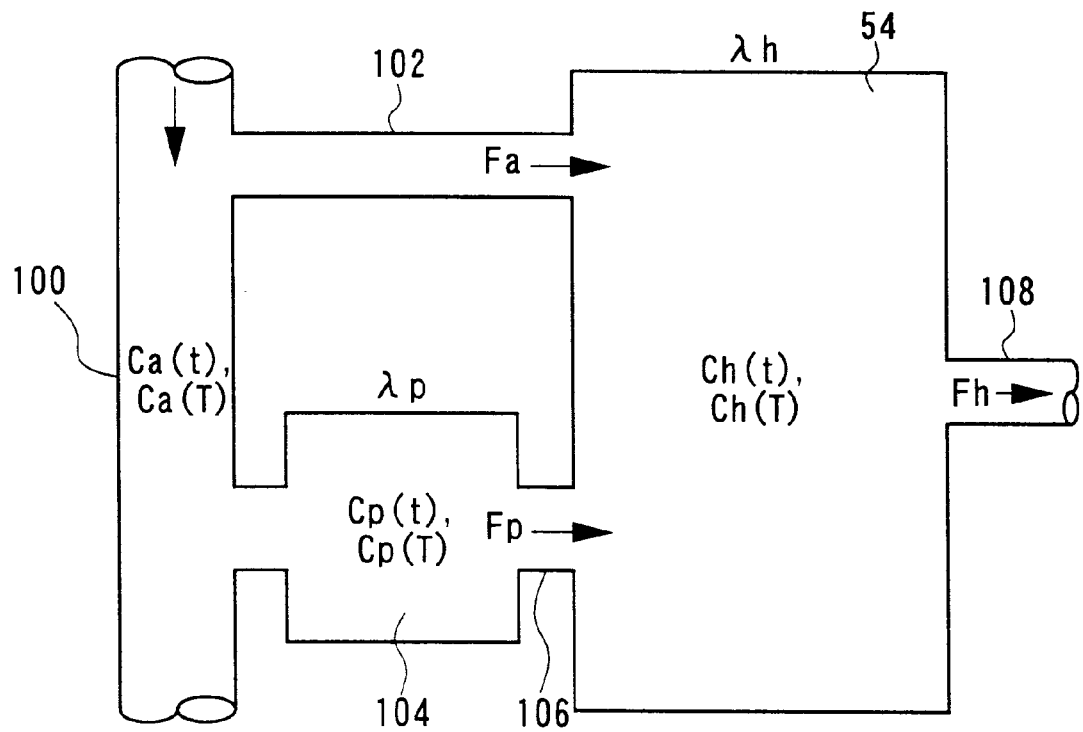
FIG. 5 shows a schematic diagram of the liver for the purpose of computer analysis.

FIG. 5 shows a known schematic diagram in which the blood flow supplied to the liver 54 is simplified (for example, see "EIZOJOHO MEDICAL" described above). As understood from FIG. 5, the hepatic arterial blood flow amount Fa is supplied to each of the regions of liver tissue 54 from the main artery 100 via the hepatic artery 102. The portal blood flow amount Fp is supplied to each of the regions of liver tissue 54, which resides in the venous blood flow fed from the main artery 100 via the portal vein 106 after passing through the portal internal organs 104 such as the stomach, the intestine, the pancreas, and the spleen. In this case, the ratio of hepatic arterial blood flow amount Fa to portal blood flow amount Fp is Fa/Fp≈⅓ in average. The hepatic arterial blood flow amount Fa and the portal blood flow amount Fp pass through the regions of liver tissue 54, and they are fed as the hepatic venous blood flow amount Fh to the hepatic vein 108. The unit of each of the blood flow amounts Fa, Fp, Fh is an amount (cc) of blood flowing through and unit volume (100 cc) per 1 minute.

The relationship represented by the following expression (1) holds concerning the respective blood flow amounts Fa, Fp, Fh.

$$Fh = Fa + Fp \tag{1}$$

As described above, the xenon concentration Ch(t) has been obtained for each of the regions of liver tissue 54 of the specimen 12 by using the X-ray CT system 14.

The xenon concentration Ca(t) in the blood flow in the main artery 100 shown in FIG. 5, i.e., the xenon concentration in the arterial blood flow flowing into the hepatic arterial blood flow amount Fa and the portal internal organs 104 is deduced from the xenon concentration in the end-expiration gas, and hence it can be calculated from the xenon concentration having been measured by using the concentration-measuring sensor 48.

On this assumption, it has been revealed that the time-dependent change in xenon concentration Ch(t) of each for each region of liver tissue 54 resides according to Fick's principle, as represented by the following expression (2), and thus it is represented by the value obtained such that the product of the hepatic venous blood flow amount Fh, the xenon concentration Ch(t) of each region of liver tissue, and the reciprocal (1/$\lambda$h) of the partition coefficient is subtracted from the sum of the product of the hepatic arterial blood flow amount Fa and the xenon concentration Ca(t) in the hepatic arterial blood flow and the product of the portal blood flow amount Fp, the xenon concentration Cp(t) in the portal internal organs 104, and the reciprocal (1/$\lambda$p) of the partition coefficient.

$$dCh(t)/dt = Fa \cdot Ca(t) + Fp \cdot Cp(t)/\lambda p - Fh \cdot Ch(t)/\lambda h \tag{2}$$

The partition coefficients $\lambda$p and $\lambda$h represent the ratios between the xenon concentration in the tissue and the xenon concentration in the blood in the portal internal organs 104 and the liver 54 respectively.

Concerning expression (2), the xenon concentration Cp(t) in the portal internal organs 104 cannot be measured, and hence it should be artificially eliminated from expression (2).

In this case, it has been revealed that the following expression (3) is obtained according to the Fick's principle taking the portal internal organs 104 into consideration. That is, the time-dependent change of the xenon concentration Cp(t) of the portal internal organs 104 is represented by the value obtained such that the product of the portal blood flow amount Fp, the xenon concentration Cp(t) of the portal internal organs 104, and the reciprocal of the partition coefficient (1/$\lambda$p) is subtracted from the product of the portal blood flow amount Fp and the xenon concentration Ca(t) in the hepatic arterial blood flow.

$$dCp(t)/dt = Fp \cdot Ca(t) - Fp \cdot Cp(t)/\lambda p \tag{3}$$

When expression (3) is solved for the xenon concentration Cp(t) in the portal internal organs 104, it is understood that the xenon concentration Cp(t) is represented by the following expression (4) containing the definite integral. In expression (4), the symbol x represents time.

$$Cp(t)=Fp\cdot \int Ca(x)\cdot \exp\{(-Fp/\lambda p)(t-x)\}dx \qquad (4)$$

In expression (4), the domain of the definite integral is [0, t].

Expression (2) is substituted by expression (4) to determine the xenon concentration Ch(T) of the liver tissue. Thus, as shown in the following expression (5), it is deduced that the xenon concentration Ch(T) is represented by the sum of the definite integrals.

$$Ch(T)=Fa\int Ca(t)\cdot \exp\{(-Fh/\lambda h)(T-t)\}dt +Fp(Fp/\lambda p)\int$$
$$[\int Ca(x)\cdot \exp\{(-Fp/\lambda p)(t-x)\}dx]\cdot \exp\{(-Fh/\lambda p)(T-t)\}dt \qquad (5)$$

In expression (5), the interval of the definite integral of the first term on the right side is [0, T]. In the double integral of the second term on the right side, the interval of an definite integral for the infinitesimal time dx is [0, t], and the interval of the definite integral for an infinitesimal time dt is [0, T].

In expression (5), the approximate solutions for the hepatic arterial blood flow amount Fa and the portal blood flow amount Fp can be determined for each region of tissue (as represented by each picture element) of liver tissue 54 by means of the least squares method while assuming that there is given $\lambda h=\lambda p$. The ratio of the flows can be calculated for each region of tissue. The portion, in which the value of the ratio satisfies Fa/Fp≈⅓, is considered to be highly possibly a normal tissue. The portion, in which the value of the ratio is deviated to increase or decrease, is considered to be highly possibly an abnormal area of tissue. In general, it is acknowledged that there is no area of tissue in which only the arterial blood flow flows. Therefore, the tissue (site), in which only arterial blood flow flows, can be estimated, for example, to be a tissue (site) in which an abnormal tissue such as a malignant tumor exists.

Figure 6:
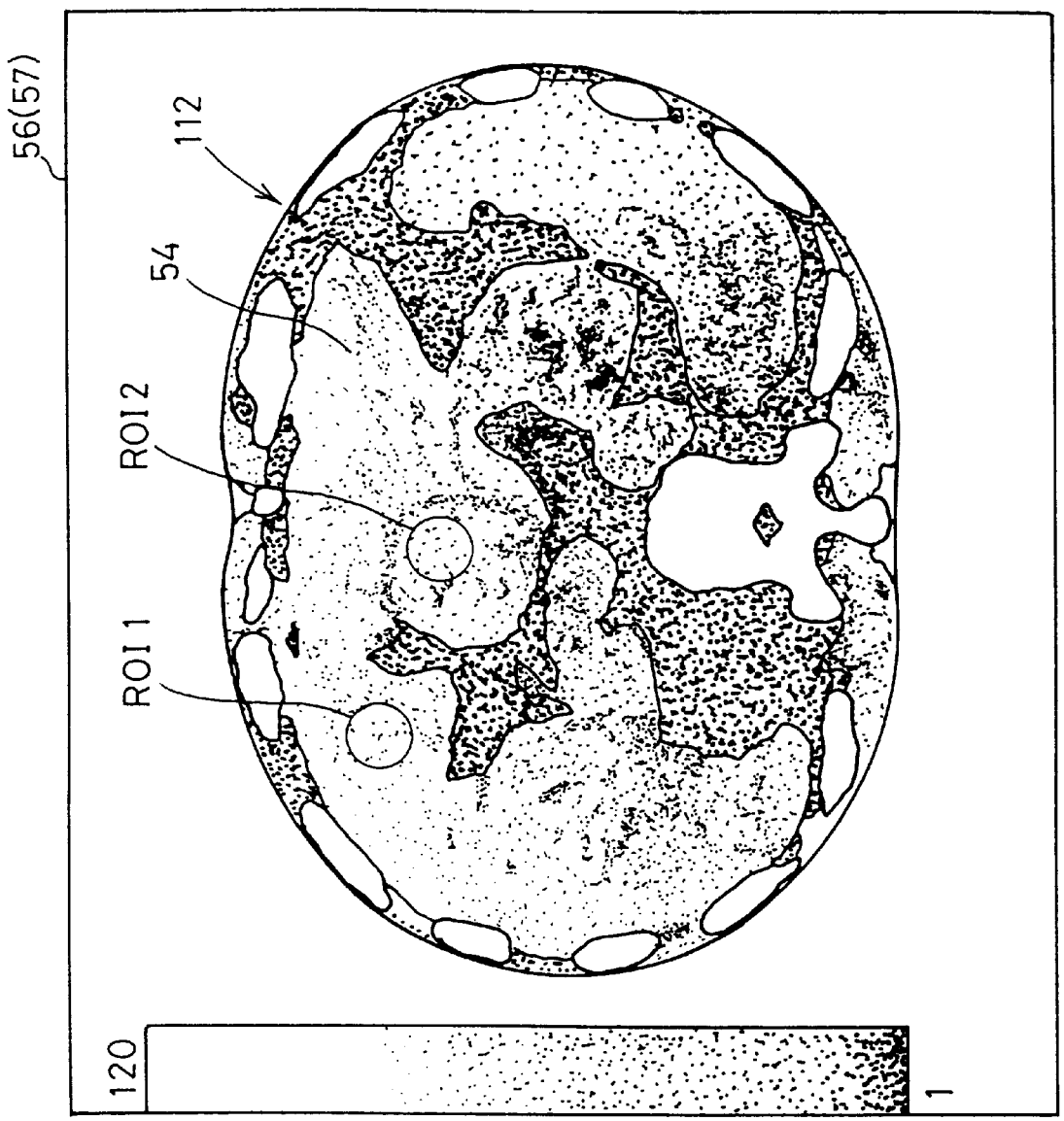
FIG. 6 shows a monochromatic illustration depicting a tomographic image of a portion including the liver.

Next, a method for analyzing the region of interest ROI in the liver 54 will be specifically explained below. FIG. 6 shows an output image 112 displayed in monochromatic illustration on the display unit 56 or on the hard copy 57 obtained by using the X-ray CT system 14, the output image 112 including the tomographic image of the liver 54 photographed in the step S4. In FIG. 6, an indication ranging from a value of 1 to a value of 120 depicted at the left end represents the CT value, i.e., the value of the Hounsfield unit [HU]. For example, two regions of interest ROI1 and ROI2, which are now intended to be analyzed, are set in desired sites or positions of the liver 54 in the output image 112 by using the operation console 52 (see the positions or regions indicated by circles in FIG. 6). The region of interest ROI can be set in an arbitrary size and at an arbitrary position.

Figure 7:
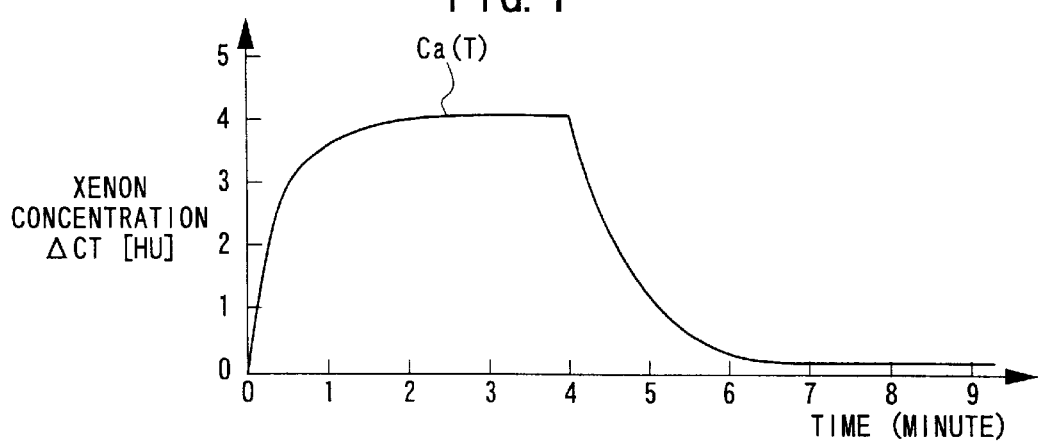
FIG. 7 shows a characteristic curve illustrating the change in xenon concentration in the main artery.
Figure 8:
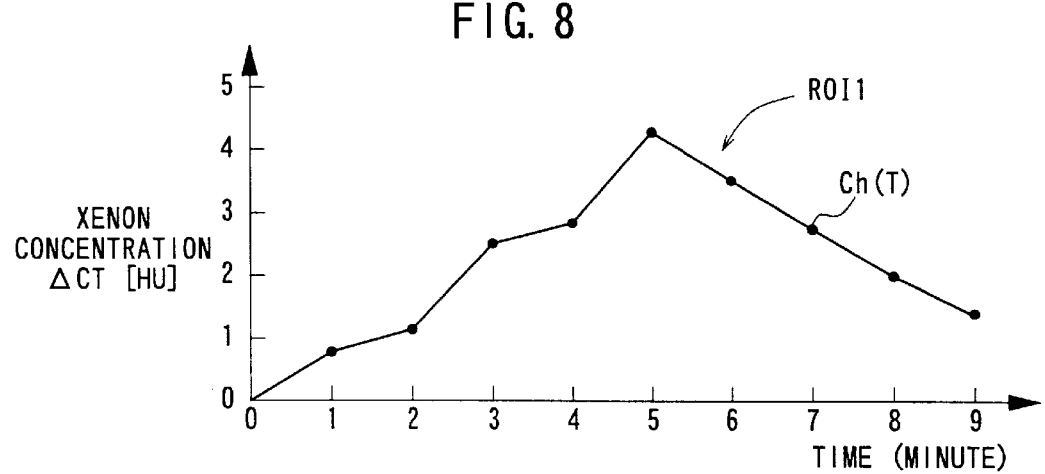
FIG. 8 shows a characteristic curve illustrating the change in xenon concentration in a certain region of interest.
Figure 9:
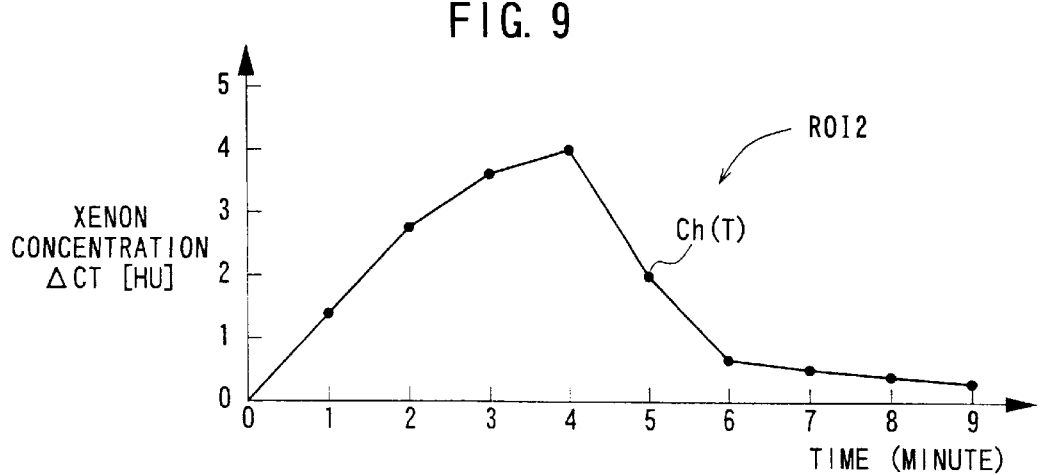
FIG. 9 shows a characteristic curve illustrating the change in xenon concentration in another region of interest.

FIG. 7 shows the change (measured value) of xenon concentration Ca(T) in the main artery 100 measured on the basis of the xenon concentration in the expiration gas. FIG. 8 shows an example of the change (measured value) of xenon concentration Ch(T) of the liver tissue of the region of interest ROI1. FIG. 9 shows an example of the change (measured value) of xenon concentration Ch(T) of the liver tissue of the region of interest ROI2. It is noted that the change of xenon concentration Ch(T) in the region of interest ROI2 shown in FIG. 9 is changed approximately in synchronization with the change of xenon concentration Ca(T) in the main artery 100 shown in FIG. 7. It is noted that the change of xenon concentration Ch(T) in the region of interest ROI1 shown in FIG. 8 is changed with delay with respect to the change of xenon concentration Ca(T) in the main artery 100 shown in FIG. 7.

Figure 10:
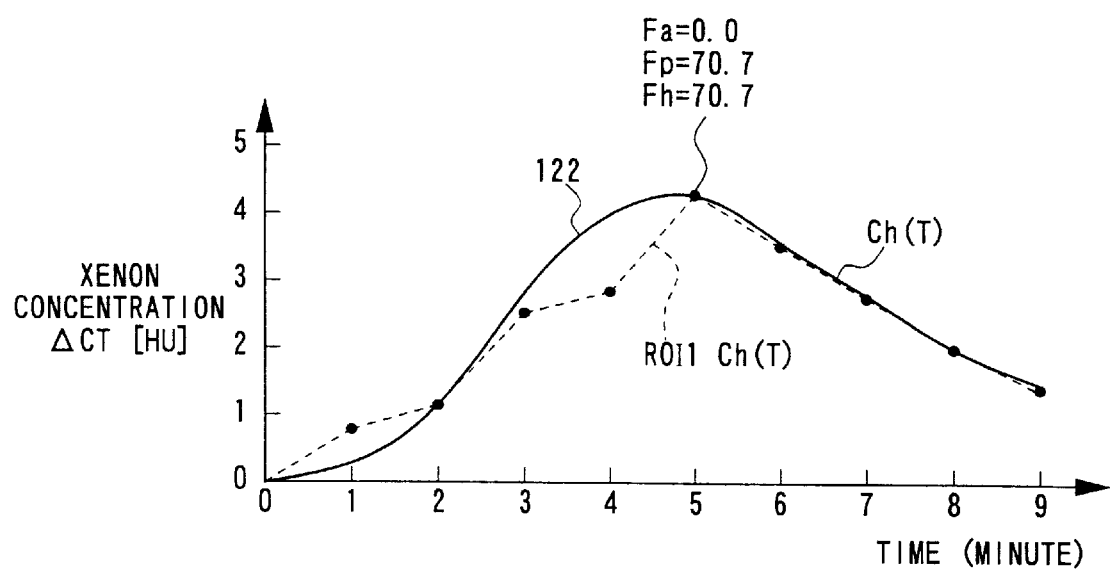
FIG. 10 shows a characteristic curve obtained by making approximation for the characteristic curve shown in FIG. 8.

In FIG. 10, reference numeral 122 indicates an approximate characteristic in which the xenon concentration Ch(T) in the region of interest ROI1 is determined with reference to the expression (2) by means of the least square method.

Figure 11:
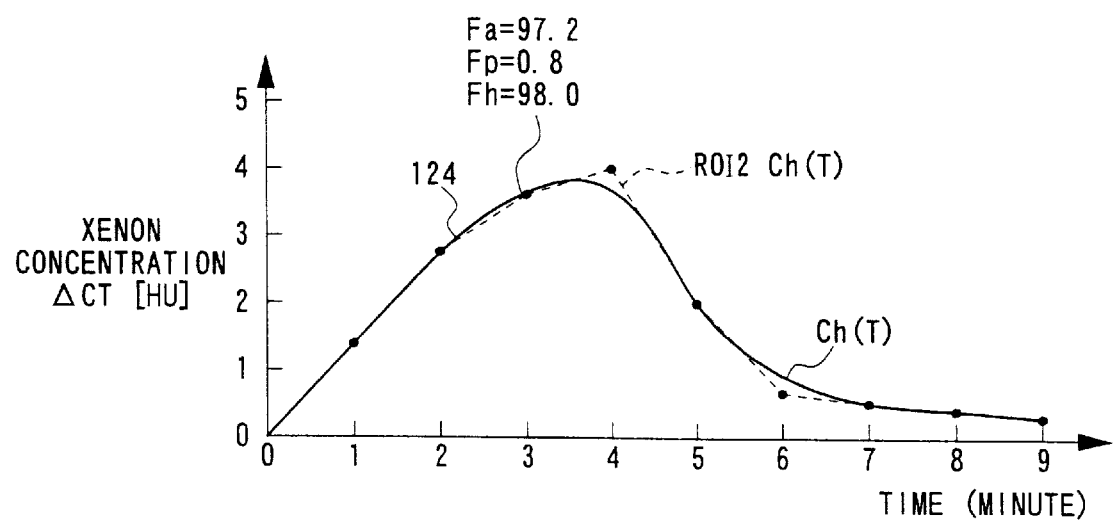
FIG. 11 shows a characteristic curve obtained by making approximation for the characteristic curve shown in FIG. 9.

On the other hand, in FIG. 11, reference numeral 124 indicates an approximate characteristic in which the xenon concentration Ch(T) in the region of interest ROI2 is determined with reference to expression (2) by means of the least squares method. FIGS. 7 to 11 are displayed on the display unit 56.

The approximate characteristic 122 shown in FIG. 10 is determined while assuming that the portal blood flow amount Fp is Fp=70.7, the hepatic arterial blood flow amount Fa is Fa=0.0, and the hepatic venous blood flow amount Fh is Fh=70.7.

The approximate characteristic 124 shown in FIG. 11 is determined while assuming that the portal blood flow amount Fp is Fp=0.8, the hepatic arterial blood flow amount Fa is Fa=97.2, and the hepatic venous blood flow amount Fh is Fh=98.

According to the approximate characteristic 122 shown in FIG. 10, it is understood that almost all of the blood amounts flowing through the region of interest ROI1 are hepatic arterial blood flow amounts Fa. On the other hand, according to the approximate characteristic 124 shown in FIG. 11, it is understood that almost all of the blood amounts flowing through the region of interest ROI2 are portal blood flow amounts Fp.

As described above, the hepatic arterial blood flow amount Fa and the portal blood flow amount Fp can be determined in a divided manner for each of the picture elements (each of the regions of tissue) of the liver 54 of the specimen 12.

Figure 12:
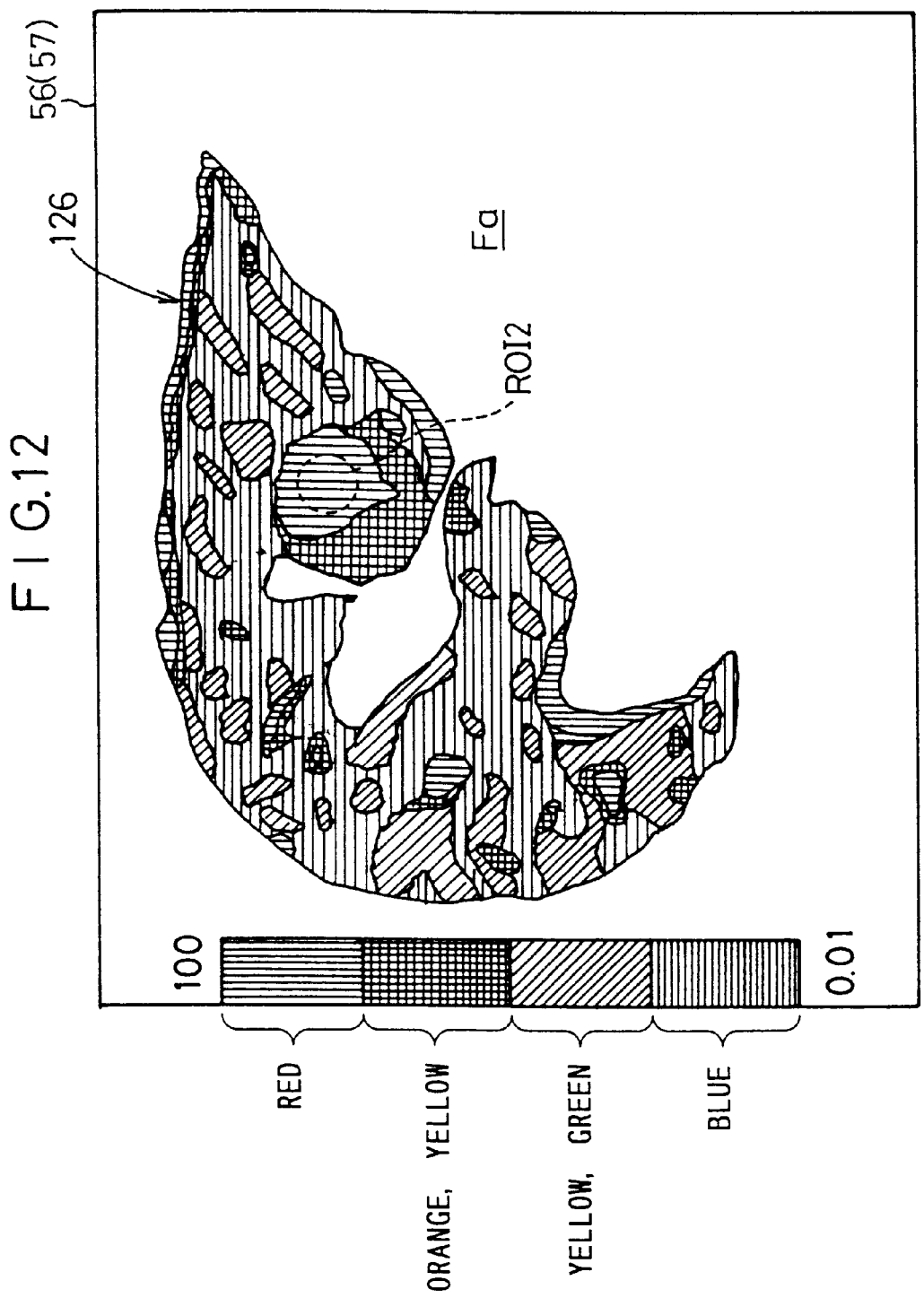
FIG. 12 shows a color illustration depicting an artery map display of the liver.
Figure 13:
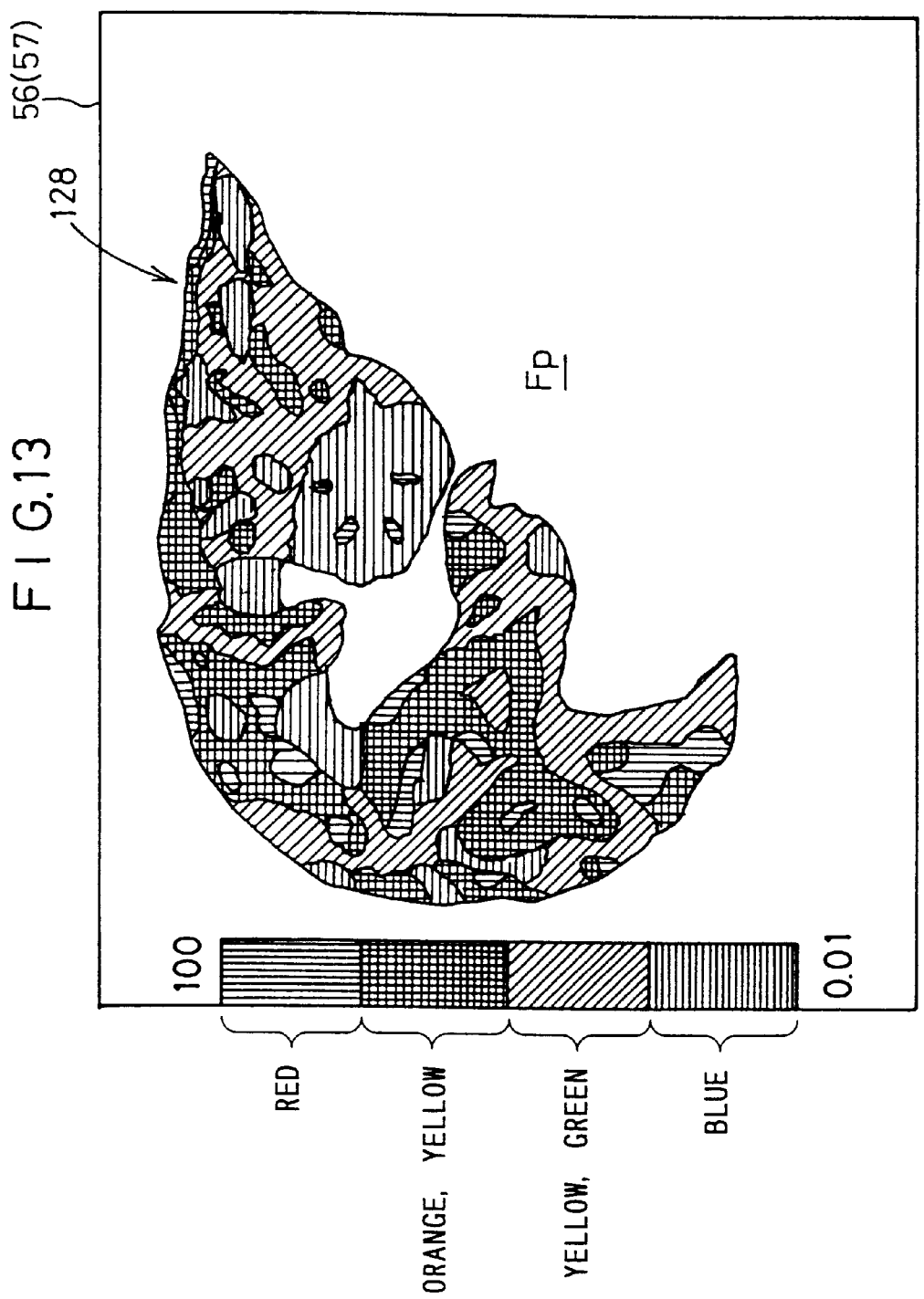
FIG. 13 shows a color illustration depicting a portal map display of the liver.
Figure 14:
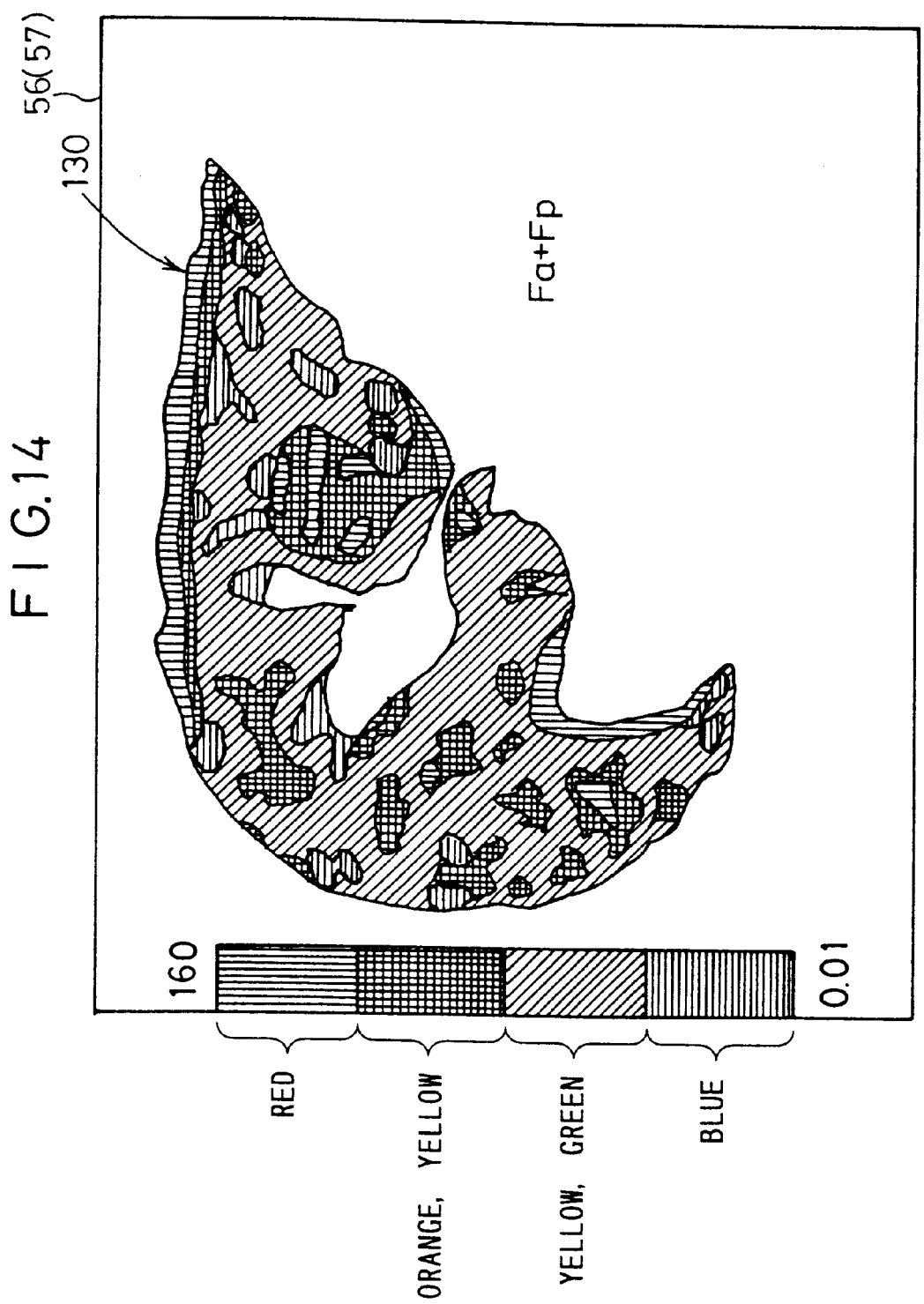
FIG. 14 shows a color illustration depicting a hepatic blood flow map of the liver.

FIG. 12 schematically and illustratively shows a color-displayed map 126 of the hepatic arterial blood flow amount Fa (also referred to as an "arterial map"). In FIG. 12, the indication ranging from a value of 0.01 to a value of 100 depicted at the left end indicates the value of the blood flow amount [cc/100 cc-tissue/min]. According to the map of the hepatic arterial blood flow amount Fa shown in FIG. 12, it is understood at a glance that almost all portions corresponding to the region of interest ROI2 are red, and almost all of the blood amounts flowing through the tissue in the region of interest ROI2 are only hepatic arterial blood flow amounts Fa. It is postulated that any abnormal tissue such as a malignant tumor exists in the site of the region of interest ROI2. FIG. 13 shows a color-displayed map 128 of the portal blood flow amount Fp (also referred to as "portal map"). FIG. 14 shows a color-displayed map 130 of the hepatic venous blood flow amount Fh (also referred to as "hepatic blood flow map").

The arterial map 126, the portal map 128, and the hepatic blood flow map 130 pertaining to the liver 54 have not been hitherto present. It is judged that extremely interesting results are obtained from a viewpoint of diagnosis.

According to the embodiment described above, the mixed gas supply apparatus 16 and the X-ray CT system 14 can be used to measure the hepatic arterial blood flow amount Fa and the portal blood flow amount Fp of the liver 54 of the specimen 12, and it is possible to make a color display in relation to the hepatic arterial blood flow amount Fa and the portal blood flow amount Fp corresponding to the results of the measurement.

Figure 3:
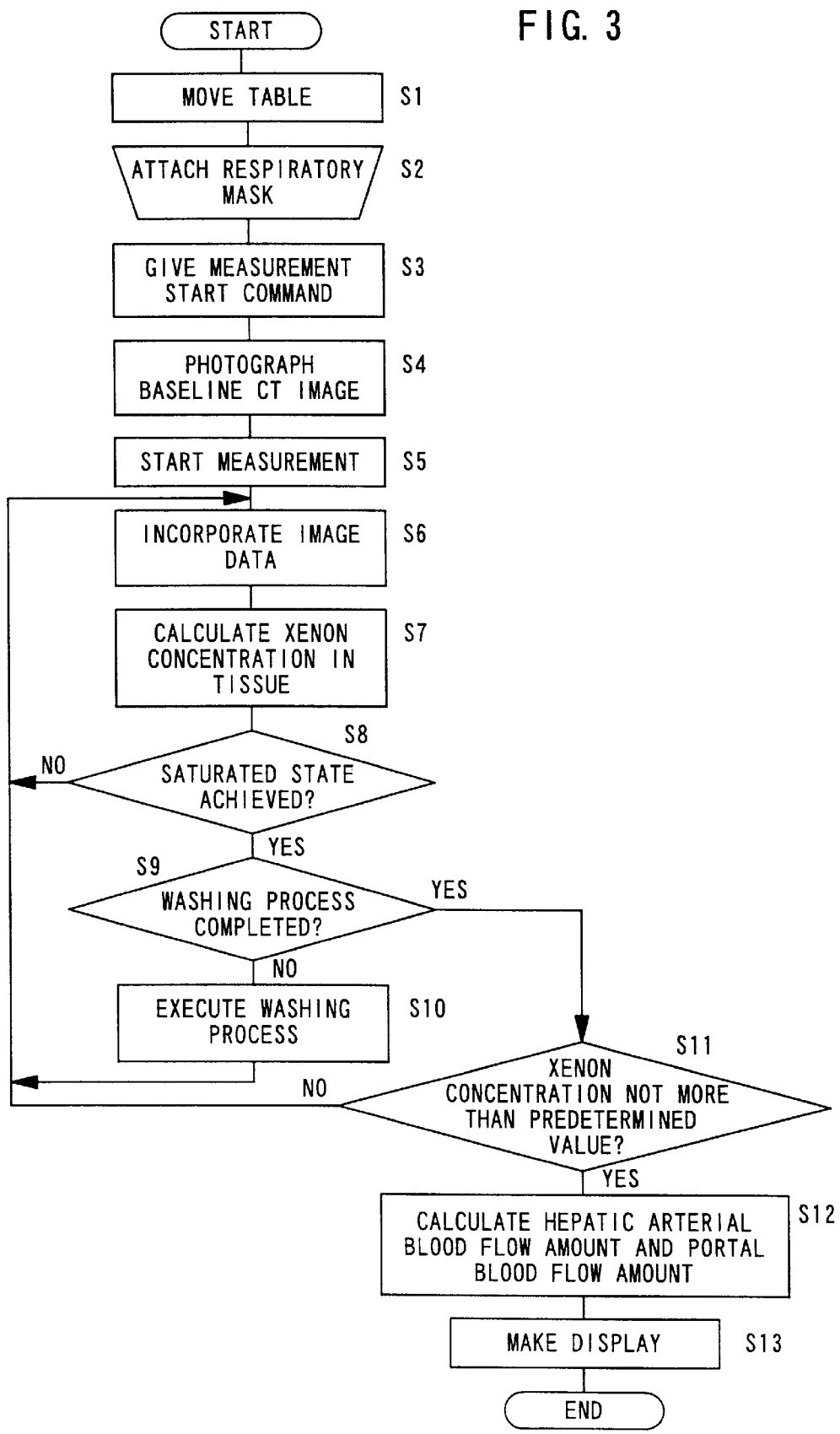
FIG. 3 shows a flow chart to be used to explain the operation of the embodiment of the present invention.

In the embodiment described above, the completion of the xenon gas inhalation process is judged on the basis of the saturation of the xenon concentration in the expiration gas (see step S8 in the flow chart shown in FIG. 3), and the completion of the xenon gas-washing process performed by changing over to inhalation of air is judged on the basis of the fact that the xenon concentration is not more than a predetermined value (see the step S11 in flow chart shown in FIG. 3). However, the inventor of this application also has discovered the fact that an improved time management can be attained, wherein the inhalation process is completed in about 4 minutes, and the washing process is completed in about 5 minutes, in order to measure the hepatic arterial blood flow amount Fa and the portal blood flow amount Fp of the liver 54 of the specimen 12.

Figure 15:
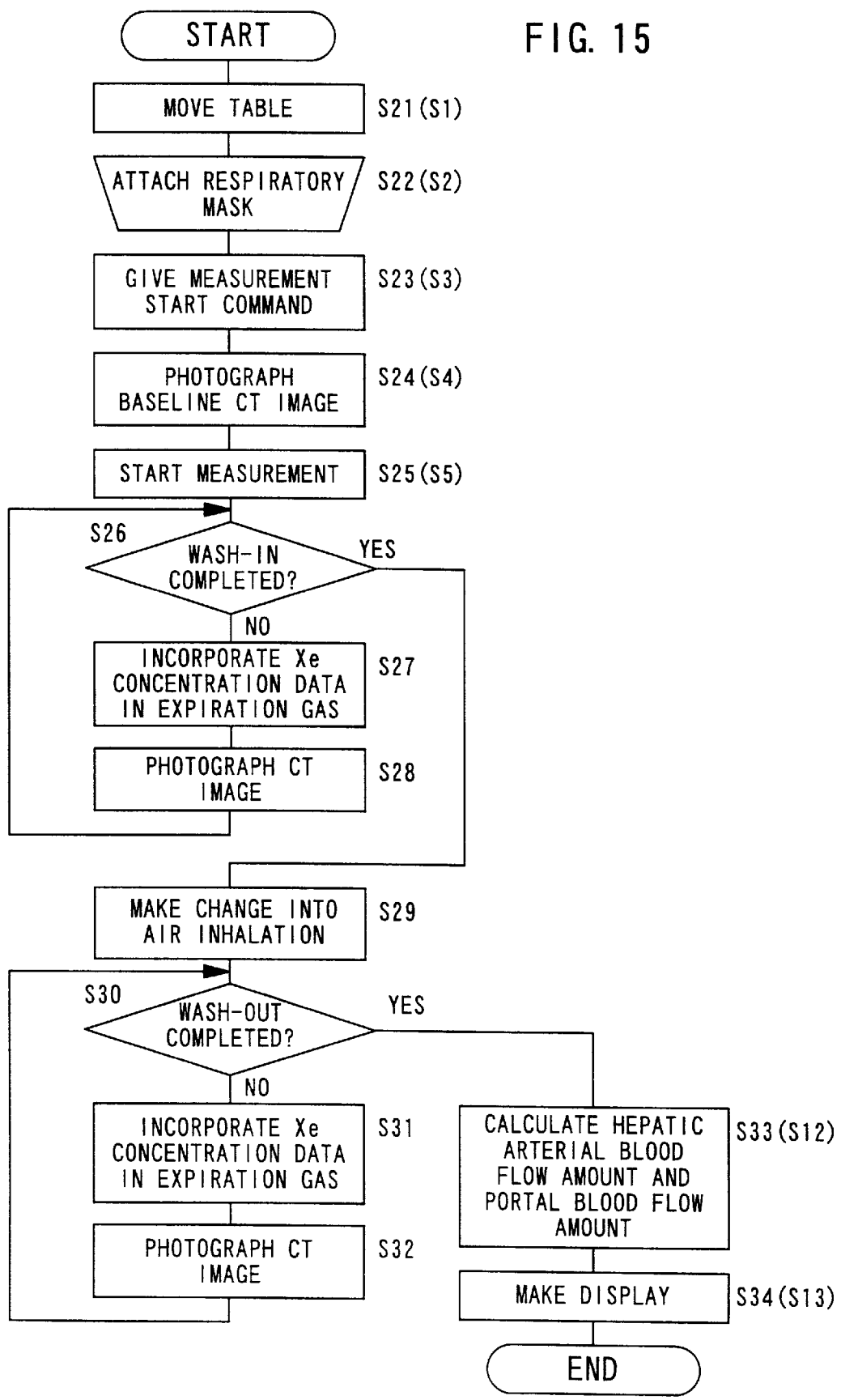
FIG. 15 shows a flow chart to be used to explain the operation of another embodiment of the present invention.

FIG. 15 shows a flow chart in which the measurement is managed along with time. Explanation will be made below with reference to the flow chart. In the flow chart shown in FIG. 15, process steps corresponding to the process steps in the flow chart shown in FIG. 3 are indicated by parentheses affixed to the flow chart shown in FIG. 15.

At first, as shown in FIG. 4, the movable table 22 is moved in the direction of arrow B in a state in which the specimen 12 is placed on the specimen-placing stand 24. The movable table 22 is stopped at a position at which the liver 54 of the specimen 12 can be photographed to obtain a tomographic image (step S21).

Subsequently, as shown in FIG. 4, the respiratory mask 44 is attached so that the mouth and the nose of the specimen 12 are covered therewith (step S22).

Subsequently, a measurement start command is generated (step S23), and the so-called baseline CT image is photographed by using the X-ray CT system 14 (step S24). A mixed gas of xenon gas and oxygen gas is fed from the mixed gas supply apparatus 16 to the specimen 12. Thus, the inhalation process (Wash-in) is started to begin the measurement (step S25). At the point of time in which the measurement is started, an unillustrated timer (time-measuring unit) contained in the control unit 20 starts a time measurement for a preset time of 4 minutes.

The completion of the inhalation process is confirmed by determining whether or not a time measurement of 4 minutes has been completed (step S26). The xenon concentration in the expiration gas is measured at every 40 msec until completion of the process (step S27). The CT image is photographed a total of four times at about every 1 minute, i.e., at 1 minute, 2 minutes, 3 minutes, and 4 minutes (step S28).

When the time measurement for 4 minutes has been completed (step S26: YES), air is started to be supplied to the specimen 12 in place of the mixed gas (step S29). Accordingly, the timer is operated to start a further time measurement for a preset time of 5 minutes so that the washing process (Wash-out) of the xenon gas is started.

Until the completion of the 5 minute time measurement for (step S30), the xenon concentration in the expiration gas is measured every 40 ms (step S31). The CT image is further photographed a total of five times at about every 1 minute, i.e., at 5 minutes, 6 minutes, 7 minutes, 8 minutes, and 9 minutes as counted from the start of the measurement process in the step S25 (step S32).

The washing process is completed (step S30: YES) at a point of time at which the time measurement for 5 minutes has been completed, i.e., a point of time at which the total time measurement for 9 minutes has been completed from the start of the measurement in step S25.

Subsequently, the hepatic arterial blood flow amount Fa and the portal blood flow amount Fp are calculated using expression (5) described above in accordance with the least squares method (step S33) for each picture element of the CT image, from the xenon concentration Ch(T) in the liver tissue deduced from the CT image data photographed in steps S28 and S32 and the xenon gas concentration Ca(T) in the arterial blood flow deduced from the xenon gas concentration data in the expiration gas measured in steps S27 and S31.

Thus, for example, the color-displayed map (arterial map) 126 of the hepatic arterial blood flow amount Fa shown in FIG. 12, the color-displayed map (portal map) 128 of the portal blood flow amount Fp shown in FIG. 13, and the color-displayed map (hepatic blood flow map) 130 of the hepatic venous blood flow amount Fh shown in FIG. 14 are displayed in the same manner as in step S13, and are used for performing diagnosis (step S34).

As explained above, according to the present invention, it is noticed that when xenon gas as an inert gas is introduced into the artery through the lung of the specimen, the xenon concentration in the liver tissue is determined from the xenon concentration in the hepatic arterial blood flow and the xenon concentration in the portal blood flow. Change in the xenon concentration in the liver tissue of the specimen is measured (detected) by making generating and displaying a plurality of respective picture elements using the X-ray CT system, so that the hepatic arterial blood flow amount and the portal blood flow amount are determined for each of the picture elements obtained thereby. Accordingly, it is possible to measure (detect) the portal blood flow amount and the arterial blood flow amount of each of the respect regions of liver tissue. Further, the liver tissue represented by each of the picture elements can be easily distinguished as to whether it is a tissue in which portal blood flow dominantly flows or it is a tissue in which hepatic arterial blood flow dominantly flows.

According to the present invention, a tomographic image of the liver, which is displayed by using picture elements obtained by the X-ray CT system, is displayed (preferably displayed as different color illustrations) while substantially seperating such picture elements into a map showing making separation into the map of the hepatic arterial blood flow and a map showing the flow of the portal blood flow on the basis of the results of the distinction obtained as described above. Thus, the present invention enhances the possibility of contributing to the diagnosis of the liver based on the hepatic blood flow.

That is, according to the present invention, the hepatic arterial blood flow amount and the portal blood flow amount can be measured in a form which is suitable for diagnosis. Further, according to the present invention, it is possible to easily detect the portal blood flow amount and the hepatic arterial blood flow amount for each of the regions of liver tissue. Furthermore, according to the present invention, the regions of liver tissue can be displayed (preferably displayed as color illustrations) while seperating the display into regions of liver tissue through which the portal blood flow flows and regions of liver tissue through which the arterial blood flow flows.

It is a matter of course that the present invention is not limited to the embodiments described above, and the present invention may be embodied in other various forms without deviating from the gist or essential characteristics of the present invention.

What is claimed is:

1. A method for measuring a hepatic blood flow amount, comprising the steps of:

detecting a change in xenon concentration by supplying a mixed gas of xenon gas and oxygen gas to a lung of a specimen for a certain period of time using a gas inhalator so that said change in xenon concentration in respective regions of liver tissue of said specimen is detected by generating picture element data corresponding to said respective regions using an X-ray CT system;

calculating blood flow amounts based on said picture element data to determine a hepatic arterial blood flow amount and a portal blood flow amount in each of said respective regions by using a processing unit, on the basis of the fact that said xenon concentration in said liver tissue is determined by a xenon concentration in a hepatic arterial blood flow and a xenon concentration in a portal blood flow; and displaying on a display unit tomographic images of said liver as represented by said plurality of picture elements obtained by said X-ray CT system, said tomographic images comprising a hepatic arterial blood flow map and a portal blood flow map, wherein said hepatic arterial blood flow map shows the hepatic arterial blood flow amount in each of said respective regions of liver tissue, and said portal blood flow map shows the portal blood flow amount in each of said respective regions of liver tissue.

2. The method according to claim 1, wherein said mixed gas is a mixed gas of a ratio of 30% of xenon gas and 70% of oxygen.

3. The method according to claim 1, wherein an inhalation period, which is a period of time to supply said mixed gas to said lung of said specimen for said certain period of time, is about 4 minutes.

4. The method according to claim 3, wherein a washing period, which follows the inhalation period of about 4 minutes, is about 5 minutes.

5. The method according to claim 1, further comprising, following said step of calculating said blood flow amounts, the steps of diagnosing that a portion of said liver tissue is normal if a ratio between said hepatic arterial blood flow amount and said portal blood flow amount in said portion is about ⅓, and diagnosing that a portion of said liver tissue is abnormal if the ratio in said portion is substantially greater or less than about ⅓.

6. The method according to claim 1, wherein a display form in said step of displaying is a display form in which said hepatic arterial blood flow amount and said portal blood flow amount are displayed using different colors.

7. An apparatus for measuring a hepatic blood flow amount, comprising:

a gas inhalator for supplying a mixed gas of xenon gas and oxygen gas to a lung of a specimen;

an X-ray CT system for detecting a change in xenon concentration in respective regions of liver tissue of said specimen while generating picture element data corresponding to said respective regions;

a control unit for controlling said gas inhalator and said X-ray CT system, wherein said control unit operates said gas inhalator so that said mixed gas is inhaled by said specimen for a certain period of time, and determines a hepatic arterial blood flow amount and a portal blood flow amount in each of said respective regions from said picture element data while referring to an expression in which said xenon concentration in said liver tissue is determined by a xenon concentration in a hepatic arterial blood flow and a xenon concentration in a portal blood flow; and a display unit for displaying tomographic images of said liver as represented by said plurality of picture elements obtained by said X-ray CT system, said tomographic images comprising a hepatic arterial blood flow map and a portal blood flow map, wherein said hepatic arterial blood flow map shows the hepatic arterial blood flow amount in each of said respective regions of liver tissue, and said portal blood flow map shows the portal blood flow amount in each of said respective regions of liver tissue.

8. The apparatus according to claim 7, wherein said mixed gas is a mixed gas of a ratio of 30% of xenon gas and 70% of oxygen.

9. The apparatus according to claim 7, wherein an inhalation period, which is a time for supplying said mixed gas to said lung of said specimen for said certain period of time, is about 4 minutes.

10. The apparatus according to claim 9, wherein a washing period after said inhalation period of about 4 minutes is about 5 minutes.

11. The apparatus according to claim 7, wherein said control unit diagnoses that a portion of said liver tissue is normal if a ratio between said hepatic arterial blood flow amount and said portal blood flow amount in said portion is about ⅓, and diagnoses that a portion of said liver tissue is abnormal if the ratio in said portion is substantially greater or less than about ⅓.

12. The apparatus according to claim 7, wherein said display form on said display unit is a display form in which said hepatic arterial blood flow amount and said portal blood flow amount are displayed using different colors.

13. The apparatus according to claim 7, wherein said expression provides said xenon concentration Ch(T) in said liver tissue in accordance with the following equation:

$$Ch(T) = Fa \int Ca(t) \cdot \exp\{(-Fh/\lambda h)(T-t)\} dt + Fp(Fp/\lambda p) \int [\int Ca(x) \cdot \exp\{(-Fp/\lambda p)(t-x)\} dx] \cdot \exp\{(-Fh/\lambda p)(T-t)\} dt$$

wherein T represents a measurement time, Fa is said hepatic arterial blood flow amount, Ca(t) and Ca(x) are said xenon concentration in said hepatic arterial blood flow wherein t and x represent a passage of time, λp is a ratio between a xenon concentration in portal internal organ tissue and a xenon concentration in blood, and λh is a ratio between said xenon concentration in said liver tissue and said xenon concentration in blood, and wherein an interval of a definite integral of a first term on a right side of said equation is [0, T], an interval of a definite integral for an infinitesimal time dx is [0, t], and an interval of a definite integral for an infinitesimal time dt is [0, T] in a double integral of a second term on the right side of said equation.

* * * * *